United States Patent [19]

Nepras et al.

[11] Patent Number: 5,840,985
[45] Date of Patent: Nov. 24, 1998

[54] PROCESS FOR THE CONVERSION OF FATTY AMIDES TO AMINES

[75] Inventors: Marshall J. Nepras, Burlington, Wis.; Randal J. Bernhardt, Antioch; Cathy J. Sporer, Lindinhurst, both of Ill.

[73] Assignee: Stepan Company, Northfield, Ill.

[21] Appl. No.: 683,707

[22] Filed: Jul. 18, 1996

[51] Int. Cl.⁶ .................................................. C07C 209/50
[52] U.S. Cl. .......................................................... 564/488
[58] Field of Search ............................................. 564/488

[56] References Cited

U.S. PATENT DOCUMENTS

| | | | |
|---|---|---|---|
| 3,190,922 | 6/1965 | Bard et al. | 260/583 |
| 3,444,204 | 5/1969 | Schutt et al. | 260/583 |
| 4,082,749 | 4/1978 | Quadback-Seeger et al. | 260/296 |
| 5,410,082 | 4/1995 | Pfirmann | 546/414 |
| 5,461,176 | 10/1995 | Sun et al. | 564/488 |

*Primary Examiner*—Allen J. Robinson
*Assistant Examiner*—Barbara Badio
*Attorney, Agent, or Firm*—McDonnell Boehnen Hulbert & Berghoff

[57] ABSTRACT

Disclosed is a process for the preparation of primary, secondary and tertiary amines with high conversion and high selectivity via low pressure catalytic hydrogenation of unsubstituted, N-substituted, and N,N-disubstituted amides. Amide hydrogenation is conducted using a catalyst system comprising copper chromite and a nucleophilic reagent, in combination with hydrogen gas. The process allows for production of amines which may be directly used as chemical intermediates in the manufacture of surfactants, quaternary ammonium compounds, bactericides, disinfectants, lubricants, petroleum additives, ion exchange resins and the like, without the need of purification, such as distillation.

33 Claims, 2 Drawing Sheets

PROCESS FOR THE CONVERSION OF FATTY AMIDES TO AMINES

BACKGROUND OF THE INVENTION

1. Field of the Invention

The present invention relates to the preparation of primary, secondary and tertiary amines with high conversion and high selectivity via low pressure catalytic hydrogenation of unsubstituted, N-substituted, and N,N-disubstituted amides. More specifically, the invention relates to amide hydrogenation conducted using a catalyst system comprising a copper salt and a nucleophilic reagent, in combination with hydrogen gas. The present invention further relates to the catalyst system.

2. Description of the Related Art

Primary, secondary and tertiary amines are important chemical intermediates widely used in the production of surfactants, quaternary ammonium compounds, bactericides, disinfectants, lubricants, petroleum additives, ion exchange resins, and the like. Such amines may be produced by the hydrogenation of amides in the presence of a hydrogenation catalyst, as represented by the reaction:

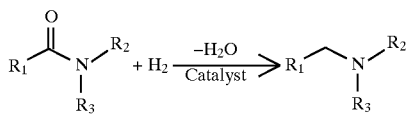

where $R_1$ is typically a $C_{10}$–$C_{22}$ hydrocarbon group and $R_2$ and $R_3$ are typically $C_1$–$C_4$ hydrocarbon groups and/or hydrogen. These hydrogenation processes are commercially unattractive due to the production of undesirable by-products, such as alcohols and mixed-amine compounds. Alcohol by-products are defined as alkyl alcohols which are generated by the reduction of intermediate aldehyde compounds formed during the amide hydrogenation. The production of these alcohols is represented by the reaction:

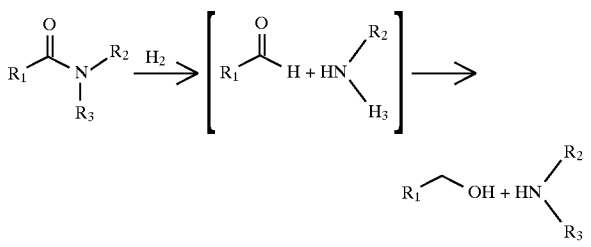

A portion of the alcohol by-products may be converted to the desired amine by the addition of an auxiliary amine, e.g., $HN(R_2)(R_3)$, as represented by the reaction:

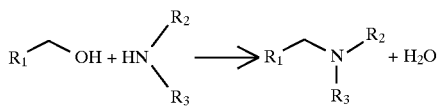

Mixed-amine by-products are defined as compounds which are produced as a result of the coupling of the desired amine with an alcohol by-product during the amide hydrogenation process. The production of these mixed-amine by-products is represented by the reaction:

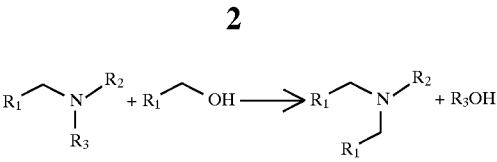

The success of any specific amide-to-amine conversion process is typically described in terms of percent conversion and percent selectivity. Percent conversion is defined as the percent of amide that is converted to reaction product. The reaction product may include the desired amine, alkyl alcohol by-products and/or mixed-amine by-products. In general, percent conversion is defined by the equation:

% Conversion=100−[(Wt. of Amide in final product)/(Initial Wt. of Amide)][100]

When the unreacted or starting amide is present in a low concentration in the final reaction product, the percent conversion is said to be high. The percent conversion does not depend on and is not indicative of the particular qualitative nature of any final product. The qualitative nature of a final product is described in terms of selectivity. The selectivity of the hydrogenation reaction is defined as the percent by weight of the desired amine present in the final reaction product. In general, percent selectivity may be defined by the equation:

% Selectivity=[(Wt. of Desired Amine obtained)/(Wt. of Desired Amine theoretical)][100]

When the desired amine is produced in a high concentration with respect to the various by-products and unreduced amide, the selectivity of the reaction is said to be high. Accordingly, the percent selectivity is dependent on and is a measure of the qualitative nature of the final product.

Due to the formation of by-products during the amide-to-amine hydrogenation process, purification by, for example, distillation, of the crude amine product is necessary to give a final amine product of suitable purity and quality for further use. Due to economic constraints, this required purification step prevents the practice of such amide hydrogenation on a commercial scale. Distillation is undesirable from both an economical and materials processing point-of-view. Thus, a strong need exists for a commercially viable amide reduction process which produces amines with high levels of conversion and selectivity, thereby eliminating the need for a distillation purification step.

Many of the amide reduction processes taught in the art suffer from low conversion yields and low overall selectivities. The processes typically involve the use of high reaction temperatures, high hydrogen gas pressures, and/or long reaction times to achieve increased selectivities and conversions. The use of high hydrogen gas pressures is undesirable for several reasons: The equipment needed to perform such reductions is very costly, reaction materials are more difficult to handle, the overall safety of hydrogenation process becomes a concern and, most importantly, reaction selectivities decrease significantly. The use of elevated temperatures to increase conversion and selectivity is undesirable, as such temperature extremes may cause product degradation, increased by-product formation and discoloration of the final amine product. As noted above, an amine product with such product degradation, by-product formation, and discoloration requires distillation prior to further use. Therefore, a need further exists for an amide reduction process which eliminates the need of high hydrogen gas pressures and/or high temperatures during the amide reduction process.

Catalytic hydrogenation of amides to produce amines in the presence of a copper chromite catalyst is known to the art. U.S. Pat. No. 3,190,922, Bard et al., issued Jun. 22, 1965, describes the catalytic hydrogenation of N,N-disubstituted amides at a temperature of about 200°–350° C. and at a hydrogen gas pressure of about 200–800 p.s.i.g. The hydrogenation catalyst utilized is copper chromium oxide, in the presence of about 2–8 percent by weight of an auxiliary dialkyl amine source. The necessity of the dialkyl amine source is exemplified by the fact that conversion of amide to amine ceases to occur after a certain period of time, as compared to a reaction where the dialkyl amine source is present throughout the reduction process. Crude reaction conversions of greater than 90% are only obtainable using hydrogen gas pressures of about 400 p.s.i.g, at temperatures of about 260°C.–270° C. The reaction products produced at hydrogen gas pressures lower than about 400 p.s.i.g. require purification, i.e., distillation, in order to obtain an amine material of greater than 90% selectivity. At pressures below 400 p.s.i.g., mixed-amine by-products are typically present from about 12–19%, i.e., 81–88% selectivity.

An improvement to the above described copper chromite amide reduction technology is disclosed in U.S. Pat. No. 4,448,998, King, issued May 25, 1984. The processes disclosed is an improvement based on the use of a dual catalyst system of copper chromite and zeolite. Typically, a N,N-disubstituted amide reduction is performed at a temperature of about 200° C. to 40020 C., at a hydrogen gas pressure of about 1990–4978 p.s.i.g. This methodology allows for the omission of the auxiliary dialkyl amine source during the amide reduction, and produces the N,N-disubstituted alkylamine with about a 72% selectivity. This methodology produces crude amine compositions which contain significant amounts of undesirable starting amide material, i.e., about 8%, and substantial amounts of undesirable alcohol and mixed-mixed amine by-products, i.e., about 8% and 9% respectively. In order to find commercial utility, these materials must be purified prior to further use.

In addition to the above described copper chromite amide reduction technology, U.S. Pat. No. 5,075,505, Forquy et. al., issued Dec. 24, 1991, discloses a processes for the production of N,N-dimethyl-N-alkylamines from the corresponding amides, using a mixed catalyst system of copper oxide, copper chromite and manganese oxide. Typically, the N,N-disubstituted amides reductions are performed at a temperature of about 200° C. to 280°C., at a hydrogen gas pressure of about 145–1450 p.s.i.g., and in the presence of about 2–8% percent by weight of an auxiliary dialkyl amine source. While this methodology and catalyst system significantly lower the amount of unreduced amide (i.e. increases the % conversion) and alcohol by-products, the desired N,N-disubstituted alkylamine is produced only in about a 87–89% yield (i.e., 87–89% selectivity), along with 10–15% of undesired N-substituted-N,N-dialkylamine by-products.

Non-copper chromite catalyst systems have been used for the reduction of amides to amines in the presence of hydrogen gas. (See EP 0 268 280 A1, Dobson, et. al., published Oct. 12, 1988). These processes utilize palladium, ruthenium or rhenium supported catalysts (and combinations thereof) to effect the desired amide-to-amine reduction, in the presence of hydrogen gas. While this methodology gives high levels of conversion, hydrogen gas pressures of about 3000–4000 p.s.i.g. are necessary, at temperatures of about 200°–250° C. Additionally, U.S. Pat. No. 4,935,546, Barrault et. al., issued Jun. 19, 1990, describes the use of titanium-based mixed-metal oxide, i.e. copper, cobalt, chromium, etc., hydrogenation catalyst systems for the reduction of amides at hydrogen gas pressure of 725–1425 p.s.i.g.

Non-amide based, i.e. nitrile, catalytic hydrogenation procedures to produce primary amines are known in the art. (See Cerveny, L., Ed. Catalytic Hydrogenation in *Studies in Surface science and Catalysis*; Elsevier: Amsterdam, 1986; Vol. 27, Chapter 24.) Such catalytic hydrogenation typically produce the desired primary amine with the formation of a significant amount secondary and tertiary amines as undesirable mixed-amine by-products. Also known are catalytic hydrogenation procedures using rhodium catalysts on alumina to produce secondary amines via the reduction of nitrites. (See Galan, A. et al., *J. Org. Chem*. 56:452 (1991)). While such reductions are reported to proceed at low hydrogen gas pressures, i.e., about 15 p.s.i.g., the reaction times are about 20–30 hours, with nitrile-to-amine conversions of only about 70–85%.

Other non-hydrogenation routes are known and utilized commercially for producing N,N-dimethyl-N-alkylamines by the reaction of dimethylamine with an alkyl halogen compound, a fatty alcohol or an alpha-olefin. However, these routes suffer from the disadvantages of expensive raw materials and excessive waste disposal costs.

Given the limitations in existing amide-to-amine hydrogenation technology, a strong need exists for a commercially viable synthetic manufacturing route to primary, secondary and tertiary amines with high conversion and selectivity.

SUMMARY OF THE INVENTION

The present invention provides an improved process for the preparation of primary, secondary and tertiary amines, and mixtures thereof, via a low pressure, catalytic hydrogenation of unsubstituted, N-substituted, N,N-disubstituted amides and mixtures thereof. The improvement resides in the use of a catalyst system comprising copper chromite and a nucleophilic reagent for the hydrogenation of primary, secondary, and tertiary amides, and mixtures thereof, to the corresponding amines. The catalyst system unexpectedly provides high levels of conversion and high selectivity while allowing for the use of lower hydrogen gas pressures, standard reaction temperatures, shorter reaction times, and in some cases, omission of an auxiliary amine source, as compared to traditional copper chromite hydrogenation catalyst systems.

The present invention also relates to a catalyst system comprising copper chromite and a nucleophilic reagent. This catalyst system is used to effect the amide to amine conversion.

The present invention also provides amine compositions and methods for preparing such compositions having low or no unreduced amide (i.e. high conversion), low alcohol reaction byproducts and low amounts of mixed-amine by-products (i.e. high selectivity) for the purpose of, among others, the preparation of quaternary ammonium compounds for detergents, antimicrobial agents, disinfectants, and surfactants.

Thus, the present invention provides an economical, low-pressure, high conversion, high selectivity process for the preparation of primary, secondary and tertiary amines from the corresponding amides. The amines produced by the process of the present invention typically require no purification, i.e., distillation, to remove undesirable by-products prior to further use.

DETAILED DESCRIPTION OF THE INVENTION

Figure 1:
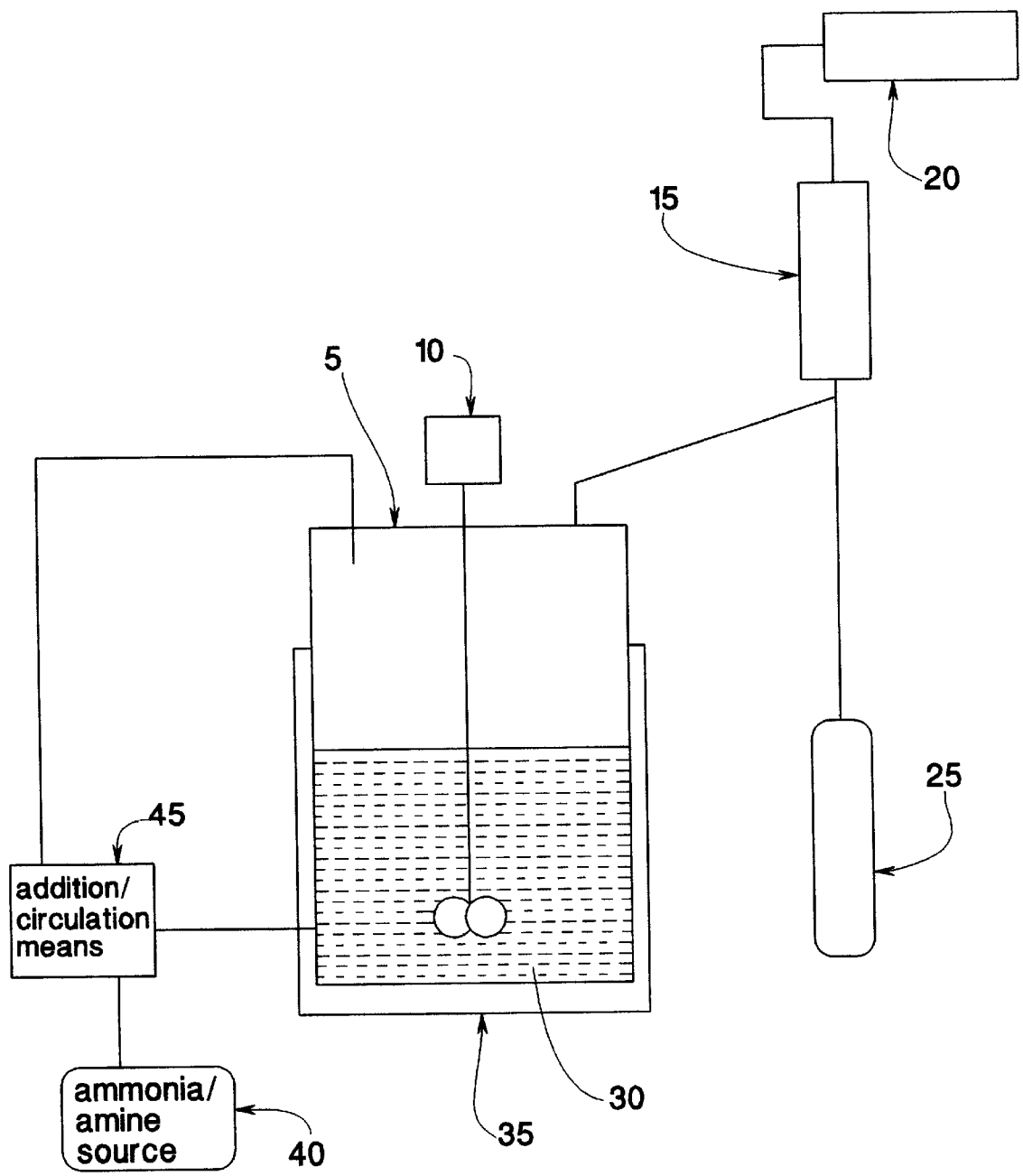
FIG. 1 is a schematic view of a closed loop amidation reactor used for carrying out the amidation process of the present invention.

In accordance with the invention, it has been surprisingly discovered that improvements to the catalytic hydrogenation of unsubstituted, N-substituted, N,N-disubstituted amides and mixtures thereof can be obtained by employing a catalyst system comprising a hydrogenation catalyst and a nucleophilic reagent.

Accordingly, the present invention comprises a process for producing primary, secondary and tertiary amines, and mixtures thereof of the formula:

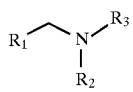

wherein $R_1$, $R_2$ and $R_3$ are independently hydrogen or saturated or unsaturated hydrocarbon groups having from about 1–28 carbon atoms, the process comprising (a) contacting or reacting an amide of the formula:

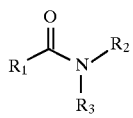

wherein $R_1$, $R_2$ and $R_3$ are independently hydrogen or saturated or unsaturated hydrocarbon groups having from about 1–28 carbon atoms, with hydrogen gas at a pressure of at least about 50 psig at a temperature of about 100°–400° C. in the presence of a catalyst system comprising a hydrogenation catalyst and a nucleophilic reagent; and (b) removing water generated by the contacting. In a preferred process of the present invention, the water generated by the contacting is continuously removed.

The reduction of the amide with hydrogen gas produces water according to the following reaction:

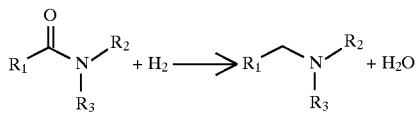

It is necessary to remove such water, in portions or continuously, to allow the hydrogenation reaction to proceed. The water may be removed by a variety of techniques known to those skilled in the art, such as, for example, the continuous circulation of hydrogen gas through the reaction mixture containing the amide and/or amine, with subsequent condensation of water away from the reaction mixture.

In a preferred embodiment of the present invention, the contacting is performed at a hydrogen gas pressure of about 50–500 psig. While 500 psig is a preferred maximum pressure, higher pressure, e.g., 700 psig or above, can be employed in the inventive process. More preferred pressures are from 75–300 p.s.i.g. Although higher pressures within this preferred pressure range may be used, such higher pressures may produce an amine at a higher rate, but with lower selectivity. In a particularly preferred embodiment of the present invention, the contacting is performed at a hydrogen gas pressure of about 75–150 p.s.i.g.

The present invention further comprises a process wherein the contacting is performed at a temperature of about 130°–290° C. In a more preferred embodiment, the contacting is performed at a temperature of about 230°–270° C.

The catalyst system is employed in the present invention in an amount sufficient to convert the amide to the amine in at least about 90% yield. More preferably, the catalyst is present in an amount sufficient to convert the amine the amide in at least about 95% yield. In other words, the catalyst system is used in an amount capable of producing the amine in greater than 90%, more preferably 95%, conversion.

In addition, the catalyst system is employed in the present invention in an amount sufficient to convert the amide to the amine with at least about 90% selectivity. More preferably, the catalyst is present in an amount sufficient to convert the amine the amide with at least about 95% selectivity. In other words, the catalyst system is used in an amount capable of producing the amine in greater than 90%, more preferably 95%, selectivity.

The present invention further comprises a process wherein the hydrogenation catalyst is present in from about 0.5–80.0 percent by weight, based on the weight of the amide. In a more preferred embodiment, the hydrogenation catalyst is present in from about 1.5–6.0 percent by weight, based on the weight of the amide. In a most preferred embodiment, the hydrogenation catalyst is present from about 2.8–3.2 percent by weight, based on the weight of the amide. In general, a higher weight percent of hydrogenation catalyst may be utilized to somewhat increase the rate of the reaction, but such an increase will not appreciably affect the quality of the final amine product. As appreciated by those skilled in the art, high weight percentages of hydrogenation catalyst (i.e. 10–80 percent by weight, based on the weight of the amide) are typically employed in fixed-bed hydrogenation reactors, where the lower weight percentages of hydrogenation catalyst (i.e., 0.5–10.0 percent by weight, based on the weight of the amide) are typically used in batch hydrogenation reactors.

Hydrogenation catalysts useful in accordance with the present invention are copper chromite and metal-promoted copper chromite. The hydrogenation catalyst used is generally in the form of a black powder, but may also be in the form of tablets or extruded granules.

A typical copper chromite hydrogenation catalyst utilized in the present invention is well known in the prior art. It is often referred to as a copper-chromium oxide hydrogenation catalyst. The preparation of this catalyst is described by Connor, et. al *J. Am. Chem. Soc.* 54, 1138 (1932) and by Adkins, *"Reactions of Hydrogen With Organic Compounds Over Copper-Chromium Oxide and Nickel Catalysts"*, University of Wisconsin Press, Madison Wis., (1937). The nature and properties of the catalyst is further described by Adkins, et. al *J. Am. Chem. Soc.,* 72, 2626 (1950). Typically, the copper chromite catalyst will contain about 33–67 percent by weight copper, based on the total weight of the catalyst, and 12–30 percent by weight chromium, based on the total weight of the catalyst. Additionally, there are a wide variety of copper chromite catalysts which are currently commercially available and are generally useful in the present invention. Examples of commercially available copper chromite catalysts include, among others, G-13A (from United Catalysts, Inc.), Cu-1800P and Cu-1808 (both from Engelhard). Some commercially available copper chromite catalysts contain metal promoters, such as barium oxide and/or manganese oxide. Examples of commercially available metal-promoted copper chromite catalysts include, among others, Cu-1132T and Cu-1186R-T (both from Engelhard). These metal-promoted copper chromite catalysts may also be used in the present invention if desired.

The present invention allows for the use of a wide variety of nucleophilic reagents. Nucleophilic reagents useful in the present invention are defined as any Lewis base compounds capable of donating electrons to an empty orbital(s) of any Lewis acid compounds. The nucleophilic reagent is present in an amount sufficient to effect greater than 90% conversion of the amide and/or greater than 90% selectivity of the amine. Such amounts are "effective amounts" of the nucleophilic reagent. In a preferred embodiment of the present invention, the nucleophilic reagent is present from about 0.01–5.0 percent by weight, based on the weight of the amide. Also, in general, a higher weight percent of the nucleophilic reagent may be utilized to somewhat increase the rate of the reaction, but such an increase will often produce an increase in the amount of alcohol by-products which are generated. The nucleophilic reagents may be in the form of anionic nucleophiles and/or neutral nucleophiles. Accordingly, the nucleophilic reagents suitable for use in the present invention are selected from the group consisting essentially of hydroxide ions (e.g., HO$^-$), alkoxide ions (e.g., RO$^-$), halides (e.g. HX; X=F, Cl, Br, I), cyanide and substituted cyanide ions (e.g., CN$^-$and RCN$^-$), thiocyanide ions (e.g., SCN$^-$), azide ions (e.g., N$_3^-$), acetate and substituted acetate ions (e.g., CH$_3$CO$_2^-$and RCH$_2$CO$_2^-$), nitrate ions (e.g., NO$_3^-$), phosphine compounds (e.g., P(R)$_3$), sulfides (e.g. S(R)$_2$), and hydrosulfide ions (e.g., HS$^-$), and the like. The preferred nucleophilic reagents are selected from the group consisting essentially of sodium methoxide, potassium methoxide, sodium ethoxide, potassium ethoxide and potassium tertbutoxide and mixtures thereof. The most preferred nucleophilic reagent of the present invention is sodium methoxide. Less preferred nucleophilic reagents include ammonia, amines, and water.

When practicing the present invention it is desirable to circulate the hydrogen gas continuously through the reaction contents to achieve optimum results. However, in a less preferred embodiment, hydrogen gas may be circulated across the top of the reaction contents.

The present invention also comprises novel amine compositions prepared from the above process containing reduced amounts of undesirable reduction by-products, such as unreduced amides, alcohol by-products and mixed-amine by-products.

Other representative amides which are useful as starting materials in the inventive process are di-, tri- and poly-amides. The reaction of an alkyl amine with, for example, the diester of adipic acid is well known, as disclosed in U.S. Pat. No. 3,417,114 to Kueski (incorporated herein by reference). It is noted therein that esters of di, tri or tetracarboxylic acids may be employed to produce the corresponding amides. These compounds contain two or more amide groups and, upon subjecting these compounds to the process of the instant invention, the amide groups are converted to the corresponding di-, tri- and poly-amines.

While the method of preparation used to generate the amides of the present invention is not critical, these amides may be prepared by a variety of techniques known to those skilled in the art. Typically, suitable unsubstituted, N-substituted, and/or N,N-disubstituted amides may be prepared by the condensation of ammonia, a primary or a secondary amine with a carboxylic acid, an ester, an acid chloride and/or an anhydride. (See *Advanced Organic Chemistry*, March, J., 4$^{th}$ ed., John Wiley, 1992, p. 417–427)

Examples of compounds useful as starting amides in the present invention include, among others, N,N-dimethylstearamide; N,N-dimethylpalmitamide; N,N-dimethyllauramide; N,N-dimethylcocoamide; N,N-dimethyloleamide; N,N,N',N'-tetramethyladipamide; N,N,N',N'-tetra-n-octyladipamide; N,N-distearylsteramide; N,N-di-n-dodecylisooctan-amide; N,N,N'N'-tetramethylamide of dimerized linoleic acid; N,N,N'N'-tetra-(2-ethylhexyl)amide of dimerized linoleic acid; N,N'-di-tetradecylpiperazine and higher molecular weight polyamides prepared form dimerized linoleic acid and piperazine.

The process of the present invention may optionally utilize an auxiliary amine. The auxiliary amine may be a primary or secondary amine having the following general formula HNR$_2$R$_3$ 

wherein R$_2$ and R$_3$ are independently hydrogen or saturated or unsaturated hydrocarbon groups having from about 1–28 carbon atoms. The use of such an auxiliary amine may aid in the transformation of alkyl alcohol by-products to the desired amine, as previously described. In one embodiment of the present invention, the amount of primary and/or secondary auxiliary amine added to the reaction mixture is about 1.0–40.0 percent by weight, based on the weight of the unsubstituted, N-substituted, and/or N,N-disubstituted amide. In a preferred embodiment of the present invention, the amount primary or secondary auxiliary amine is present from about 1–20.0 percent by weight, based on the weight of the unsubstituted, N-substituted, and/or N,N-disubstituted amide.

In the present invention, the primary or secondary auxiliary amine is contacted with the amide or amide and mixture in a continuous mode or a batch mode, i.e., the primary or secondary auxiliary amine may be introduced at once at the beginning of the hydrogenation or it may be added continuously during the course of the hydrogenation.

The present invention further comprises a process wherein the amide used for the subsequent reduction has the following general formula:

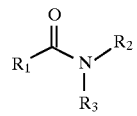

wherein R$_1$ is a saturated, unsaturated, branched, linear or cyclic hydrocarbon group having about 1–28 carbon atoms, R$_2$ and R$_3$ independently represent saturated or unsaturated, branched, linear or cyclic hydrocarbon groups having about 1–28 carbon atoms,—(CH$_2$CH$_2$0)$_n$—H, wherein n=1–100, —(CH$_2$CH(CH$_3$)0)$_n$—H, wherein n=1–100, or H, or a mixture thereof.

Further, the present invention comprises a process wherein the primary or secondary auxiliary amine has the following general formula HNR$_2$R$_3$ 

wherein R$_2$ and R$_3$ are independently H, saturated or unsaturated, branched, linear or cyclic hydrocarbon radicals of from about 1–28 carbon atoms, —(CH$_2$CH$_2$O)$_n$=—H, wherein n=1–100or —(CH$_2$CH(CH$_3$)0)$_n$—H, wherein n=1–100, or H. Optionally, mixtures of said primary or secondary amines may be employed as the anxiliary amine.

The present invention may be performed in a batch mode or in a continuous mode of operation.

All documents, e.g., patents and journal articles, cited above or below are hereby incorporated by reference in their entirety.

The preferred embodiments of the present invention are more fully illustrated by the following examples which demonstrate the improvements previously described compared to using the prior art copper chromite hydrogenation technology. The following examples are set forth for purposes of illustration only. All parts and percentages, unless otherwise stated, are by weight.

One skilled in the art will recognize that modifications may be made in the present invention without deviating from the spirit or scope of the invention. The invention is illustrated further by the following examples which are not to be construed as limiting the invention or scope of the specific procedures or compositions described herein.

General Methods of Preparation: Synthesis of Unsubstituted, N-Substituted, or N,N-Disubstituted Amides From Alkyl Esters While not critical to the present invention, the unsubstituted, N-substituted and N,N-disubstituted amides and mixtures thereof may be prepared by a variety of methods known in to the art. Additionally, many amides useful in the inventive process may be purchased as readily available commercial materials. In the present invention, the amides are prepared in a closed loop amidation reactor. FIG. 1 shows a schematic view of an example closed loop amidation reactor suitable for use in the present invention. The closed loop reactor vessel 5 is equipped with a means for agitation 10, a means for addition and circulation 45 of ammonia, a source of primary and/or a secondary amine 40, a means for heating 35, a condenser 15, a collection trap 25, and a means for providing optional vacuum 20 to the closed loop reactor vessel 5. In the practice of the invention, the closed loop reactor 5 is charged with a fatty ester, such as an alkyl methyl ester, and an amidation catalyst (both collectively represented as 30), such as one of the nucleophilic reagents previously defined. (The amine source is optionally added at once to the reactor at this stage of the reaction.) The reactor is sealed and agitation begun. If the amine source was not added at once prior to the sealing of the reactor, the amine source is added slowly to the reactor. If the amine source is a gaseous amine, the amine vapor may be continuously circulated through the reaction contents. Heating is applied to the contents of the reactor as needed to effect the desired amidation reaction with evolution, removal and collection of alcohol, such as methanol in the case of an alkyl methyl ester. After amidation is complete, the amide is optionally filtered and subsequently used for preparation of primary, secondary and tertiary amines.

General Methods of Preparation: Synthesis of Primary. Secondary or Tertiary Amines From Unsubstituted, N-Substituted, or N,N-Disubstituted Amides In accordance with the present invention, a closed loop, medium pressure hydrogenation reactor is utilized for the preparation of primary, secondary and tertiary amines via the low pressure, catalytic hydrogenation of unsubstituted, N-substituted, N,N-disubstituted amides or mixtures thereof. These amines may be prepared in the representative reactor shown schematically in FIG. 2. Each of the examples herein was performed in a 2000 ml reaction vessel.

Figure 2:
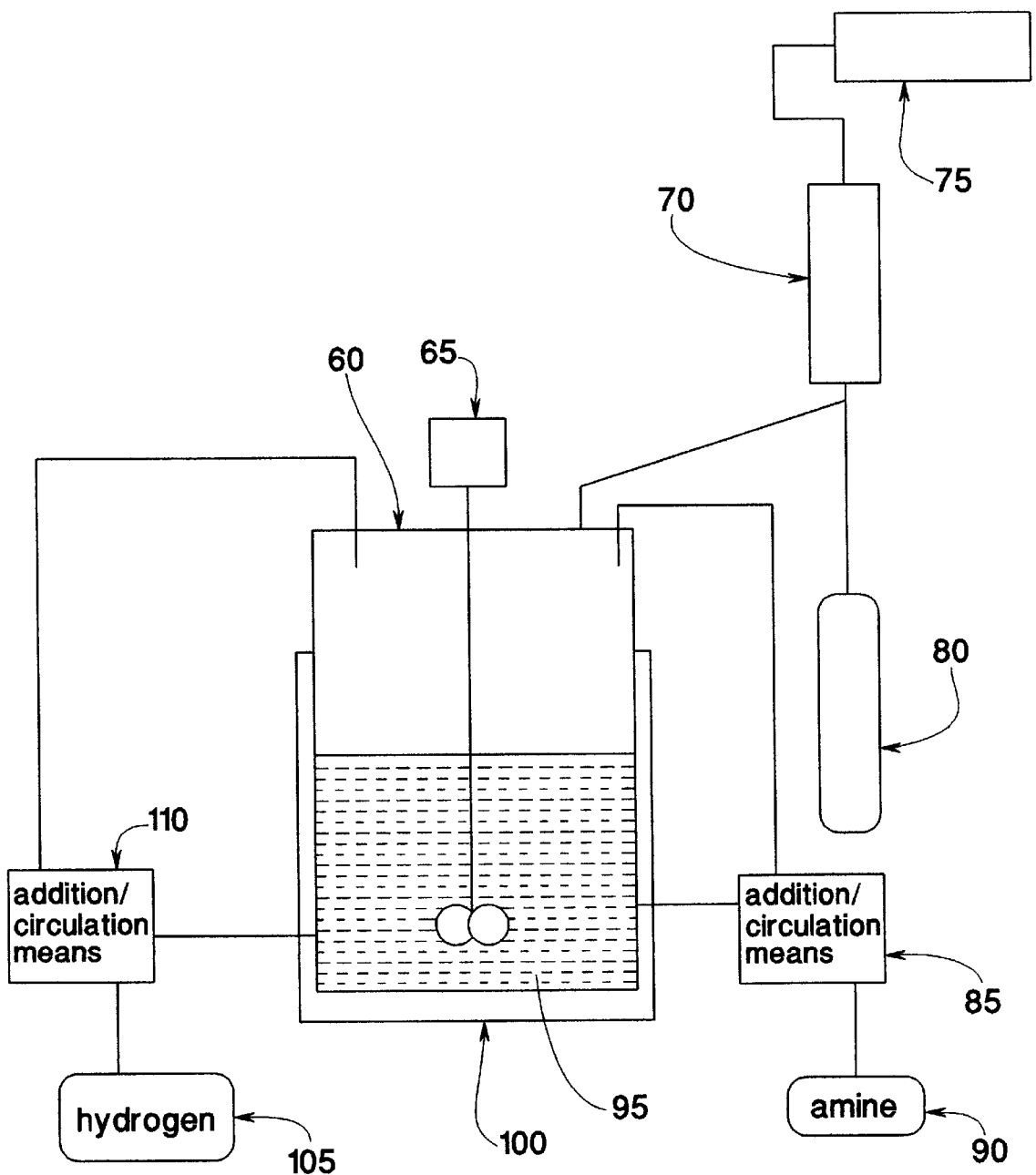
FIG. 2 is a schematic view of a closed loop amination reactor used for carrying out the amination process of the present invention.

As depicted in FIG. 2, the closed loop, medium pressure, reactor vessel 60 is equipped with a means for agitation 65, a means for addition and/or circulation 85 of the auxiliary amine from amine source 90, a means for addition and/or circulation 110 of hydrogen gas from gas source 105, a means for heating 100, a condenser 70, a water collection trap 80, and a means for providing optional vacuum 75 to the reactor. The reactor is charged with an unsubstituted, N-substituted, or N,N-disubstituted amide or a mixture thereof, a nucleophilic reagent and the hydrogenation catalyst (collectively represented by 95). (The amine source 90 may optionally be added at once to the reactor at this point.) The reactor is sealed and agitation begun. If the amine source is a gaseous amine, the amine vapor is continuously circulated through the reaction contents with the use of a pump. Heating and circulation of the hydrogen gas under pressure is conducted as needed to effect the desired amination reaction with evolution, removal and collection of water. After the reaction is completed, the desired primary, secondary or tertiary amine or mixture thereof is isolated from the hydrogenation catalyst.

The nucleophilic reagent may comprise the nucleophilic reagent which was utilized in the amidation or an additional nucleophilic reagent or a combination thereof. Further, the nucleophilic reagent may be present as residual nucleophilic reagent from the amidation. The hydrogenation catalyst may be a catalyst which has not been utilized in any previous reaction, i.e., a fresh catalyst, or the hydrogenation catalyst may be a catalyst which had been previously utilized in the processes described herein, i.e., a recycled catalyst.

EXAMPLE #1

Preparation of a Mixture of N,N-Dimethyldodecylamide and N,N-Dimethyltetradecylamide A closed loop amidation reactor is charged with about 600 g of a mixture of dodecanoic acid methyl ester and tetradecanoic acid methyl ester (a mixture of $C_{12}$ and $C_{14}$ fatty acid methyl esters) and about 11 g of sodium methoxide (NaOMe; 25 wt.% solution in methanol). The reactor is sealed, agitation is begun, and the condenser is cooled to approximately 10° C. The reactor is sequentially pressurized with nitrogen gas to about 10 psig, purged and re-pressurized with nitrogen gas three times to remove trace amounts of air. The reactor is heated to about 80°C., charged with dimethylamine (DMA) to a pressure of about 5 psig and DMA circulated through the reaction mixture at about 0.5 mL/minUte. As the reaction proceeds, methanol is collected. Methanol generation is complete in about 9 hours, the reactor is depressurized, all residual DMA sparged from the reactor with nitrogen, the temperature adjusted to ambient and the resulting N,N-diemthyldodecylamide removed from the reactor. The amide is optionally filtered to remove any trace amounts of solid particulate mater. Upon gas chromatography analysis, the amidation reaction produces the desired mixture of N,N-dimethyldodecylamide and N,N-dimethyltetradecylamide in about 98% crude yield. The amide may be further purified via reduced pressure distillation to 99+% if so desired.

Table #1 below shows a summary of several amidation samples prepared in a manner similar to Example #1. The amides produced are of the formula $R_1 C(O)NR_2R_3$ wherein $R_1$, $R_2$, and $R_3$ are defined in the table. All reactions were run under a slight dimethylamine (DMA) pressure of about 2–5 p.s.i.g., wherein the DMA was introduced in to reactor containing the alkyl ester in a continuous mode. As can be seen, the yields of the desired N,N-disubstituted amides are typically 94–99%.

TABLE 1

| Sample No. | $R_1/R_2/R_3$ | DMA Gas Pressure (psig) | DMA Flow Rate (ml/min.) | Amidation Temp. (°C.) | Amidation Catalyst (2%) | Reaction Time (hours) | Yield (%) |
|---|---|---|---|---|---|---|---|
| 1 | $C_{12-14}$/Me/Me | 5 | 0.5 | 81 | NaOMe | 9 | 94.1 |
| 2 | $C_{12-14}$/Me/Me | 2 | 0.5 | 81 | NaOMe | 5.5 | 98.43 |
| 3 | $C_{12-14}$/Me/Me | 5 | 0.5 | 82 | NaOMe | 10 | 98.28 |
| 4 | $C_{12-14}$/Me/Me | 5 | 0.5 | 83 | NaOMe | 5 | 98.65 |
| 5 | $C_{12-14}$/Me/Me | 5 | 0.5 | 81 | NaOMe | 5 | 98.43 |

EXAMPLE #2
Preparation of a Mixture of N,N-Dimethyldodecylamine and N,N-Dimethyltetradecylamine (With DMA)

The closed loop amination reactor is charged with about 800 g of a mixture of N,N-dimethyldodecylamide and N,N-dimethyltetradecylamide (a mixture of dimethyl $C_{12}$ and $C_{14}$ fatty amides), prepared according to Example #1, and about 40 g of copper chromite (fresh catalyst). The N,N-dimethyldodecylamide contains the residual sodium methoxide from the amidation reaction and no additional nucleophilic reagent is added. The reactor is sealed, agitation is begun, and the condenser is cooled to about 10° C. The reactor is sequentially evacuated to approximately −15 psig, pressurized with nitrogen gas to atmospheric pressure, pressurized with nitrogen to 20 psig, purged and re-evacuated; this sequence is performed three times. The reactor is next sequentially evacuated to approximately −15 psig, pressurized with hydrogen gas to atmospheric pressure, pressurized with hydrogen gas to about 20 psig, purged and re-evacuated; this sequence is performed two times. Finally, the reactor is pressurized to about 400 psig hydrogen gas pressure, and the hydrogen gas is circulated through the reaction contents at a rate of about 2.5 g/min. The reactor is heated to about 250° C., the reactor is charged with dimethylamine (DMA) at a rate of about 0.13 g/minute at a pressure of about 200 psig and the DMA is circulated through the reaction mixture. As the reaction proceeds, water is collected. The DMA is added to the reactor at the above rate until water evolution ceases.

After evolution of water is complete, the reactor is depressurized, all residual DMA and hydrogen gases are sparged from the reactor with nitrogen, the temperature adjusted to ambient and the resulting mixture of N,N-dimethyldodecylamine and N,N-dimethyltetradecylamine removed from the reactor. The amine is separated from the reaction catalyst via filtration. Gas chromatography analysis indicated that the desired mixture of N,N-dimethyldodecylamine and N,N-dimethyltetradecylamine was produced in about 95% conversion and about 95% selectivity (i.e., about 5% of mixed-amine and alkyl alcohol by-products).

EXAMPLE #3
Preparation of a Mixture of N,N-Dimethyldodecylamine and N,N-Dimethyltetradecylamnine (With DMA)

The closed loop amination reactor is charged with about 800 g of a mixture of N,N-dimethyldodecylamide and N,N-dimethyltetradecylamide, prepared according to Example #1 and about 40 g of copper chromite (fresh catalyst). The amide mixture contains residual sodium methoxide from the amidation reaction and no additional nucleophilic reagent is added. The reactor is sealed, agitation is begun, and the condenser is cooled to about 10° C. The reactor is sequentially evacuated to approximately −15 psig, pressurized with nitrogen gas to atmospheric pressure, pressurized with nitrogen to about 20 psig, purged and re-evacuated; this sequence is performed three times. The reactor is next sequentially evacuated to approximately −15 psig, pressurized with hydrogen gas to atmospheric pressure, pressurized with hydrogen gas to about 20 psig, purged and re-evacuated; this sequence is performed two times. The reactor is then pressurized to about 400 psig hydrogen gas pressure. The hydrogen gas is circulated through the reaction contents at a rate of about 2.5 g/min. The reactor is heated to about 250° C. As the reaction proceeds, water is collected in the collection trap via condensation in the condenser.

After evolution of water is complete, the reactor is depressurized, all residual hydrogen gases are sparged from the reactor with nitrogen, the temperature adjusted to ambient and the resulting mixture of N,N-dimethyldodecylamine and N,N-dimethyltetradecylamine removed from the reactor. The amine mixture is separated from the reaction catalyst via filtration. Analysis indicated that the desired mixture of N,N-dimethyldodecylamine and N,N-dimethyltetradecylamine was produced in 95.4% conversion and 95.7% selectivity (i.e., 4.3% of alkyl alcohol and 0.2% of mixed-amine by-products).

EXAMPLE #4
Preparation of a 50:50 Mixture of N,N-Dimethyldodecylamine/N,N-Dimethyltetradecylamine (With DMA)

The closed loop amination reactor is charged with about 400 g of N,N-dimethyldodecylamide and about 400 g of N,N-dimethyltetradecylamide, each prepared according to Example #1 above and about 40 g of copper chromite (recycled catalyst). The N,N-dimethyldodecylamide/N,N-dimethyltetradecylamide mixture contains only residual sodium methoxide from the amidation reaction; no additional nucleophilic reagent is added. The reactor is sealed, agitation is begun, and the condenser is cooled to about 10° C. The reactor is sequentially evacuated to approximately −15 psig, pressurized with nitrogen gas to atmospheric pressure, pressurized with nitrogen to about 20 psig, purged and re-evacuated; this sequence is performed three times. The reactor is next sequentially evacuated to approximately −15 psig, pressurized with hydrogen gas to atmospheric pressure, pressurized with hydrogen gas to about 20 psig, purged and re-evacuated; this sequence is performed two times. The reactor is pressurized to about 150 psig hydrogen gas pressure, and the hydrogen gas is circulated through the reaction contents at a rate of about 2.5 g/min. The reactor is heated to about 250° C., the reactor is charged with dimethylamine (DMA) at a rate of about 0.13 g/minute at a pressure of about 150 psig and the DMA is circulated through the reaction mixture. As the reaction proceeds, water is collected. The DMA is added to the reactor at the above rate until water evolution ceases.

After evolution of water is complete, the reactor is depressurized, all residual DMA and hydrogen gases are sparged from the reactor with nitrogen, the resulting amine mixture removed from the reactor. The amine mixture is separated from the on catalyst via filtration. Analysis indicated that the desired N,N-dyldodecylamine/N,N-dimethyltetradecylamine mixture was produced in about 99% conversion and 99% selectivity. Only trace amounts of unreduced amide, alkyl alcohol by-products and mixed-amine by-products were present in the crude amine mixture.

Table #2 below shows a summary of several amination samples prepared in a manner similar to Example #2 on either an 800 g or 14 kg scale. Samples 1–4 were performed on the 14 kg scale. The amines produced are of the formula $R_1CH_2NR_2R_3$ wherein $R_1$, $R_2$, and $R_3$ are defined as shown below. For each sample preparation, the nucleophilic reagent is 0.05% by weight, based on the weight of the starting amide, of residual sodium methoxide used in the preceding amidation reaction. All reactions were run wherein the DMA was introduced to the amide in a continuous mode. Fresh copper chromite hydrogenation catalyst was utilized for Samples 1–4 and Samples 9–10. Recycled copper chromite catalyst was utilized for Samples 5–8. as can be seen, the crude yields of the desired tertiary amines are about 91–99%.

residual sodium methoxide from the amidation reaction and no additional nucleophilic reagent is added. (This nucleophilic-free amide was prepared by washing the amide with dilute phosphoric acid followed by distillation.) The reactor is sealed, agitation is begun, and the condenser is cooled to about 10° C. The reactor is sequentially evacuated to approximately −15 psig, pressurized with nitrogen gas to atmospheric pressure, pressurized with nitrogen to about 20 psig, purged and re-evacuated; this sequence is performed three times. The reactor is next sequentially evacuated to approximately −15 psig, pressurized with hydrogen gas to atmospheric pressure, pressurized with hydrogen gas to about 20 psig, purged and re-evacuated; this sequence is performed two times. The reactor is pressurized to about 400 psig hydrogen gas pressure. The hydrogen gas is circulated through the reaction contents at a rate of about 2.5 g/min. The reactor is heated to about 160° C., the reactor is charged with dimethylamine (DMA) at a rate of about 0.1 g/minute at a pressure of about 400 psig and the DMA is circulated through the reaction mixture. As the reaction proceeds, water is collected. The DMA is added to the reactor at the above rate until water evolution ceases.

TABLE 2

| Sample No. | $R_1/R_2/R_3$ | $H_2$ Gas Pressure | $H_2$ Gas Flow Rate (scfm) | DMA Flow Rate (g/kg amide/hr.) | Amination Temp. (°C.) | Catalyst amount (% $2CuO,Cr_2O_3$ by weight of reaction mixture) | Reaction Time (hrs.) | Selectivity (%) |
|---|---|---|---|---|---|---|---|---|
| 1 | $C_{12-14}$/Me/Me | 150 | 3 | 19.4 | 250 | 2.5 | 12 | 91 |
| 2 | $C_{12-14}$/Me/Me | 150 | 1.5 | 19.4 | 250 | 5 | 17 | 99 |
| 3 | $C_{12-14}$/Me/Me | 150 | 3.5 | 13.8 | 250 | 5 | 19 | 93 |
| 4 | $C_{12-14}$/Me/Me | 150 | 3.5 | 2.8 | 250 | 5 | 17 | 94 |
| 5 | $C_{12-14}$/Me/Me | 150 | 3.5 | 15 | 250 | 2.3 | 8 | 96 |
| 6 | $C_{12-14}$/Me/Me | 150 | 3.5 | 15 | 250 | 2.3 | 8 | 93 |
| 7 | $C_{12-14}$/Me/Me | 150 | 3.5 | 15 | 250 | 2.3 | 12 | 99 |
| 8 | $C_{12-14}$/Me/Me | 150 | 3.5 | 15 | 250 | 2.3 | 11 | 98 |
| 9 | $C_{12-14}$/Me/Me | 400 | 3.5 | 15 | 250 | 2.3 | 3 | 95 |
| 10 | $C_{12-14}$/Me/Me | 400 | 3.5 | 15 | 250 | 2.3 | 4 | 96 |

TABLE 3

Tertiary Amine Conversion and Selectivity*

| Sample # | $R_1\text{-}N(R_2)(R_3)$ | $R_1\text{-}CH_2\text{-}N(R_2)(R_1)$ | $R_1\text{-}C(O)\text{-}N(R_2)(R_3)$ | Alkyl Alcohols |
|---|---|---|---|---|
| 1 | 91 | 1.5 | 5.7 | 1.7 |
| 2 | 99 | 1.3 | 0.0 | 0.04 |
| 3 | 93 | 3.3 | 2.0 | 1.3 |
| 4 | 94 | 1.5 | 0.0 | 5.0 |
| 5 | 96 | 2.3 | 1.2 | 0.0 |
| 6 | 93 | 2.8 | 0.5 | 3.6 |
| 7 | 99 | 1.3 | 0.0 | 0.0 |
| 8 | 98 | 1.2 | 0.5 | 0.0 |
| 9 | 95 | 4.8 | 0.0 | 0.0 |
| 10 | 96 | 2.0 | 0.0 | 1.8 |

*$R_1/R_2/R_3$ as defined in Table 2. All values are percent by weight.

Comparative Example #1
Preparation of N,N-Dimethyldodecylamine (No nucleophilic reagent)

The closed loop amination reactor is charged with about 617 g of a mixture of N,N-dimethyldodecylamide and N,N-dimethyltetradecylamide prepared essentially according to Example #1 and about 31 g of copper chromite (fresh catalyst). The N,N-dimethyldodecylamide contains no After evolution of water is complete, the reactor is depressurized, all residual DMA and hydrogen gases are sparged from the reactor with nitrogen, the temperature adjusted to ambient and the resulting N,N-dimethyldodecylamine removed from the reactor. The amine is separated from the reaction catalyst via filtration. Gas chromatography analysis indicated that the desired amine mixture was produced in 99.9% conversion but with only 79% selectivity (i.e., 21% of mixed-amine by-products were present).

Without the use of the nucleophilic reagent, the hydrogenation of amides at low pressures and standard temperatures produces an amine product with high conversion but unacceptably low selectivity. Such materials require purification prior to further usage.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed:

1. A process for preparing an amine of the formula:

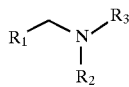

wherein $R_1$, $R_2$ and $R_3$ are independently hydrogen or saturated or unsaturated hydrocarbon groups having from about 1–28 carbon atoms; the process comprising
(a) contacting an amide of the formula:

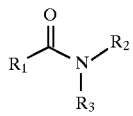

wherein $R_1$, $R_2$ and $R_3$ are defined above,
with hydrogen gas at a pressure of about 50–500 psig at a temperature of about 100°–400° C. in the presence of a catalyst system comprising a hydrogenation catalyst and a nucleophilic reagent; and
(b) removing water generated by the contacting.

2. A process according to claim 1, wherein $R_1$ is a saturated or unsaturated hydrocarbon group of 6–24 carbon atoms and $R_2$ and $R_3$ are independently hydrogen or saturated or unsaturated hydrocarbon groups having from about 1–12 carbon atoms.

3. A process according to claim 2, wherein $R_1$ is a saturated or unsaturated hydrocarbon group of 8–22 carbon atoms and $R_2$ and $R_3$ are independently hydrogen or saturated or unsaturated hydrocarbon groups having from about 1–6 carbon atoms.

4. A process according to claim 1, wherein the contacting is performed at a hydrogen gas pressure of about 75–300 psig.

5. A process according to claim 4, wherein the contacting is performed at a hydrogen gas pressure of about 75–150 psig.

6. A process according to claim 1, wherein the contacting is performed at a temperature of about 130°–290° C.

7. A process according to claim 6, wherein the contacting is performed at a temperature of about 230°–270° C.

8. A process according to claim 1, wherein the hydrogenation catalyst is present at from about 0.5–6.0 weight percent, based on the weight of the amide.

9. A process according to claim 8, wherein the hydrogenation catalyst is present at from about 1.5–4.0 weight percent, based on the weight of the amide.

10. A process according to claim 9, wherein the hydrogenation catalyst is present at from about 2.8–3.2 weight percent, based on the weight of the amide.

11. A process according to claims 10, wherein the hydrogenation catalyst is copper chromite.

12. A process according to claim 1, wherein the nucleophilic reagent is present in an amount sufficient to produce the amine in greater than 90% conversion.

13. A process according to claim 12, wherein the nucleophilic reagent is present in an amount sufficient to produce the amine in greater than 95% conversion.

14. A process according to claim 1, wherein the nucleophilic reagent is present in an amount sufficient to produce the amine in greater than 90% selectivity.

15. A process according to claim 14, wherein the nucleophilic reagent is present in an amount sufficient to produce the amine in greater than 95% selectivity.

16. A process according to claim 1, wherein the nucleophilic reagent is present at from about 0.01–5.0 weight percent, based on the weight of the amide.

17. A process according to claim 1, wherein the nucleophilic reagent is a hydroxide ion, an alkoxide ion, a halide, a cyanide ion, a substituted cyanide ion, a thiocyanide ion, an azide ion, an acetate ion, a substituted acetate ion, a nitrate ion, a phosphine, a sulfide, a hydrosulfide ion, ammonia, or a mixture thereof.

18. A process according to claim 17, wherein the nucleophilic reagent is sodium methoxide, potassium methoxide, sodium ethoxide, potassium ethoxide, potassium tert-butoxide or a mixture thereof.

19. A process according to claim 18, wherein the nucleophilic reagent is sodium methoxide.

20. A process according to claim 1, wherein the hydrogen gas is circulated through the amide.

21. A process for preparing an amine of the formula:

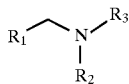

wherein $R_1$, $R_2$ and $R_3$ are independently hydrogen or saturated or unsaturated hydrocarbon groups having from about 1–28 carbon atoms;
the process comprising
(a) contacting an amide of the formula:

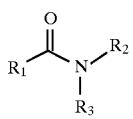

wherein $R_1$, $R_2$ and $R_3$ are defined above,
with hydrogen gas at a pressure of about 50–500 psig at a temperature of about 100°–400° C. in the presence of a catalyst system comprising a hydrogenation catalyst and a nucleophilic reagent, and in the presence of an auxiliary primary or secondary amine; and
(b) removing water generated by the contacting.

22. A process according to claim 21, wherein $R_1$ is a saturated or unsaturated hydrocarbon group of 6–24 carbon atoms and $R_2$ and $R_3$ are independently hydrogen or saturated or unsaturated hydrocarbon groups having from about 1–12 carbon atoms.

23. A process according to claim 22, wherein $R_1$ is a saturated or unsaturated hydrocarbon group of 8–22 carbon atoms and $R_2$ and $R_3$ are independently hydrogen or saturated or unsaturated hydrocarbon groups having from about 1–6 carbon atoms.

24. A process according to claim 21, wherein the contacting is performed at a hydrogen gas pressure of about 75°–300 psig.

25. A process according to claim 21, wherein the contacting is performed at a temperature of about 130°–290° C.

26. A process according to claim 21, wherein the hydrogenation catalyst is present at from about 0.5–6.0 weight percent, based on the weight of the amide.

27. A process according to claims 21, wherein the hydrogenation catalyst is copper chromite.

28. A process according to claim 21, wherein the nucleophilic reagent is present from about 0.01–5.0 weight percent, based on the weight of the amide.

29. A process according to claim 28, wherein the nucleophilic reagent is sodium methoxide, potassium methoxide, sodium ethoxide, potassium ethoxide or potassium tert-butoxide or a mixture thereof.

30. A process according to claim 29, wherein the nucleophilic reagent is sodium methoxide.

31. A process according to claim 21, wherein the hydrogen gas is continuously circulated through the amide.

32. A process according to claim 21, wherein the auxiliary primary or secondary amine has the following general formula $$HNR_2R_3$$

wherein $R_2$ and $R_3$ are independently hydrogen or saturated or unsaturated hydrocarbon groups having from about 1–28 carbon atoms.

33. A process according to claim 32, wherein the auxiliary primary or secondary amine is present from about 1.0–40.0 weight percent, based on the weight of the amide.

* * * * *